United States Patent
Ueno

(10) Patent No.: US 9,084,815 B2
(45) Date of Patent: Jul. 21, 2015

(54) METHOD FOR TREATING DAMAGE INDUCED BY AN ANTI-TUMOR AGENT, TREATING MUCOSITIS AND TREATING TUMOR

(75) Inventor: Ryuji Ueno, Montgomery, MD (US)

(73) Assignee: SUCAMPO AG, Zug (CH)

(*) Notice: Subject to any disclaimer, the term of this patent is extended or adjusted under 35 U.S.C. 154(b) by 0 days.

(21) Appl. No.: 12/882,794

(22) Filed: Sep. 15, 2010

(65) Prior Publication Data

US 2011/0064748 A1 Mar. 17, 2011

Related U.S. Application Data

(60) Provisional application No. 61/243,019, filed on Sep. 16, 2009.

(51) Int. Cl.
*A01N 43/16* (2006.01)
*A61K 31/35* (2006.01)
*A61K 45/06* (2006.01)
*A61K 31/352* (2006.01)
*A61K 31/713* (2006.01)
*A61K 39/395* (2006.01)

(52) U.S. Cl.
CPC .............. *A61K 45/06* (2013.01); *A61K 31/352* (2013.01); *A61K 31/713* (2013.01); *A61K 39/395* (2013.01)

(58) Field of Classification Search
None
See application file for complete search history.

(56) References Cited

U.S. PATENT DOCUMENTS

| | | | |
|---|---|---|---|
| 5,073,569 A | 12/1991 | Ueno et al. | |
| 5,166,174 A | 11/1992 | Ueno et al. | |
| 5,212,324 A | 5/1993 | Ueno | |
| 5,221,763 A | 6/1993 | Ueno et al. | |
| 5,302,617 A | 4/1994 | Ueno | |
| 5,438,075 A * | 8/1995 | Skubitz et al. | 514/563 |
| 5,739,161 A | 4/1998 | Ueno | |
| 6,242,485 B1 | 6/2001 | Ueno | |
| 6,414,016 B1 * | 7/2002 | Ueno | 514/456 |
| 2006/0281818 A1 | 12/2006 | Ueno et al. | |
| 2009/0012165 A1 | 1/2009 | Ueno | |

FOREIGN PATENT DOCUMENTS

| | | |
|---|---|---|
| EP | 0 454 429 A2 | 10/1991 |
| JP | 4-330015 A | 11/1992 |
| JP | 7-70054 A | 3/1995 |
| TW | 200642690 A | 12/2006 |
| WO | 96/03992 A1 | 2/1996 |
| WO | 01/70233 A2 | 9/2001 |
| WO | 02/89812 A1 | 11/2002 |
| WO | 2006/080549 A2 | 8/2006 |
| WO | 2006/101244 A2 | 9/2006 |

OTHER PUBLICATIONS

Ducreux et al. Effective treatment of advanced biliary tract carcinoma using 5-fluorouracil continuous infusion with cisplatin. Annals of Oncology, 9: 653-656, 1998.*
Straus et al. Cyclopentenone prostaglandins: new insights on biological activities and cellular targets. Medicinal Research Reviews, vol. 21, Issue 3, Apr. 6, 2001.*
Porter et al. Recurrent aphthous stomatitis. Critical reviews in oral biology and medicine. 1998, 9:306.*
Adrian et al. CA: a cancer journal of clinicals. vol. 30, Issue 3, May/Jun. 1980.*
Lenz et al. Extended safety and efficacy data on S-1 plus cisplatin in patients with untreated, advanced gastric carcinoma in a multicenter phase Ii study. Cancer, vol. 109, Issue 1, published online Nov. 28, 2006.*
Dorwald. Side reactions in organic synthesis. p. IX. 2006.*
Saito, S. et al., Chiryogaku, 1990, vol. 24, No. 9, pp. 117-119.
Ogura, Y. et al., Nihon Byouin Yakuzaishikai Zasshi, 2008, vol. 44, No. 8, pp. 1274-1277.
Hirata, K. et al., Research Communications in Molecular Pathology and Pharmacology, 1999, vol. 104, No. 3, pp. 243-251.
Kamisugi, K. et al., Gan to Kagakuryoho, 2008, vol. 35, No. 8, pp. 1331-1335.
Hamaguchi, T. et al., Medicina, 2005, vol. 42, No. 11, pp. 1984-1988.
Chinese Office Action for Application No. 201080041097.0 issued Jan. 14, 2013.
Ning et al.; Prevention and Management of Common ADRs Induced by Antitumor Drugs; Evaluation and Analysis of drug-use in Hospitals in China, (Dec. 31, 2007), vol. 7, No. 1; pp. 76-79.
Extended European Search Report for corresponding Application No. 10817322.0 dated May 14, 2013, 16 pages.
Peter Bright-Asare et al, 16-16 Dimethyl Prostaglandin E2 Reduces 5-Fluorouracil-Induced and Mitomycin C-Induced Gastric Mucosal Injury in the Dog, Cancer, vol. 54, No. 1, Jul. 1, 1984, pp. 28-31.
Hashimoto Shoji et al, Cytotoxicity of anti-cancer drugs to vascular endothelial cells and inhibitory effect of PGE1; Journal of Clinical Biochemistry and Nutrition, vol. 24, No. 1, 1998, pp. 13-21.

(Continued)

*Primary Examiner* — Anna Pagonakis
(74) *Attorney, Agent, or Firm* — Sughrue Mion, PLLC

(57) ABSTRACT

Disclosed is a method for treating tumor in a mammalian subject, which comprises administering a combination of (a) an anti-tumor agent and (b) a fatty acid derivative represented by the formula (I):

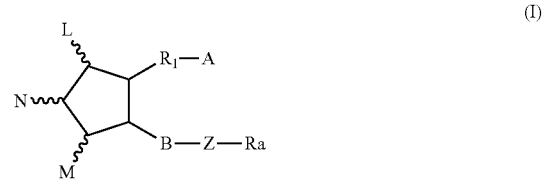

to the subject in need thereof. The application also discloses a method for treating damages, especially gastrointestinal damages including mucositis such as stomatitis induced by an anti-tumor agent, wherein the method comprises administering a fatty acid derivative of formula (I) to the subject who is receiving the anti-tumor agent.

5 Claims, No Drawings

(56) References Cited

OTHER PUBLICATIONS

Kikuchi Y et al, Adjuvant effects of prostaglandin D2 to cisplatin on human ovarian cancer cell growth in nude mice; European Journal of Cancer and Clinical Oncology, Pergamon Press Ltd., vol. 24, No. 12, Dec. 1, 1988, pp. 1829-1833.

Leport P et al; PGE restores the immune response in chemotherapy-treated, tumor-bearing mice; Life Sciences, Pergamon Press, Oxford, GB, vol. 30, No. 14, Apr. 5, 1982, pp. 1219-1223.

Ikeguchi Masahide et al.; Cisplatin combined with prostaglandin E1 chemotherapy in rat peritoneal carcinomatosis; International Journal of Cancer, John Wiley & Sons, Inc. New York, NY; US, vol. 88, No. 3, Nov. 1, 2000, pp. 474-478.

Mcclay et al.; delta 12-Prostaglandin-J2 is cytoxic in human malignancies and synergized with both cisplatin and radiation; Cancer Research, vol. 56, No. 17, Sep. 1, 1996, pp. 3866-3869.

Sasaki et al.; Antitumor activity of 13,14-dihydro-15-deoxy-delta7-prostaglandin-A1-methyl ester integrated into lipid microspheres against human ovarian carcinoma cells resistant to cisplatin in vivo; Cancer Research, vol. 59, No. 16, Aug. 1, 1999, pp. 3919-3922.

Duenas-Gonzalez A. et al.; Misoprostol prophylaxis for high-dose chemotherapy-induced mucositis: A randomized double-blind study, Bone Marrow Transplantation, vol. 17, No. 5, 1996, pp. 809-812.

Office Action issued on Mar. 31, 2014 by the European Patent Office in Application No. 10 817 322.0 (10 pages).

Communication dated Jul. 31, 2014 from the Australian Patent Office in counterpart application No. 2010296307.

Maltoni M. et al., "Topical prostaglandin E2 and chemo- and radio-induced oral mucositis: Report on 15 cases", Oncol Reports 3, Jan. 1996, p. 205-208.

Communication dated Oct. 20, 2014, issued by the Russian Patent Office in counterpart Application No. 2012114771/15.

Taiwanese Office Action issued May 8, 2015, in Application No. 099131408, 8 pages.

\* cited by examiner

METHOD FOR TREATING DAMAGE INDUCED BY AN ANTI-TUMOR AGENT, TREATING MUCOSITIS AND TREATING TUMOR

CROSS REFERENCES TO THE RELATED APPLICATIONS

This application claims priority from a provisional application filed Sep. 16, 2009 and assigned provisional Ser. No. 61/243,019. The whole contents of the provisional application are herein incorporated by reference.

TECHNICAL FIELD

The present invention relates to a pharmaceutical combination of an anti-tumor agent and a fatty acid derivative for treating tumor in a mammalian subject. The present invention also relates to a method for treating tumor in a mammalian subject. The present invention further relates to a composition and a method for treating damages, especially gastrointestinal damages including mucositis such as stomatitis induced by an anti-tumor agent.

BACKGROUND ART

Neoplastic diseases are recognized throughout the world as being serious and often life-threatening conditions. These neoplastic diseases have been and continue to be the subject of worldwide research efforts directed toward the identification of therapeutic agents which are effective in the treatment of patients suffering therefrom.

There are a variety of anti-tumor agents to treat neoplastic diseases. For example, 5-fluorouracil (hereinafter referred to as "5-FU") is an antimetabolite having a structure of pyrimidine analog, which is used as a drug in the treatment of neoplastic diseases. Its principal uses are in gastrointestinal cancer such as gastric cancer, colon cancer, rectal cancer and pancreatic cancer. Other uses are for example, in hepatic cancer, breast cancer, uterine cancer and ovarian cancer. The chemotherapy agent 5-FU acts principally as a thymidylate synthase inhibitor. Thymidylate synthase inhibitors include 5-FU, Capecitabine, Tegafur, Carmofur, Floxuridine, and so on. Tegafur is known to release 5-FU when activated in the living body. 5-FU is known to have the serious problem that the prolonged presence of 5-FU in the living body causes damages in the digestive organs such as oral cavity and intestine. Patients receiving continuous intravenous infusion of 5-FU alone often experience those damages.

Cisplatin, cisplatinum, or cis-diamminedichloroplatinum (II) (CDDP) is a platinum-based chemotherapy drug used to treat various types of cancers, including testicular tumor, bladder cancer, prostatic cancer, ovarian cancer, non-small cell lung cancer, esophageal carcinoma, cervical cancer, gastric cancer, osteosarcoma, lymphomas, and germ cell tumors. It was the first member of a class of anti-cancer drugs which now also includes carboplatin, nedaplatin and oxaliplatin. These platinum complexes react in vivo, bind to and cause crosslinking of DNA which ultimately triggers apoptosis (programmed cell death).

In general, severe side effects of those anti-tumor agents limit the dose escalation and prevent from achieving higher therapeutic effects.

In order to improve the therapeutic effect, some combinations of plural drugs which have different mechanisms and different side effects are proposed. However, more potent drugs and therapeutic method are still strongly desired such that the survival time of cancer patients is further prolonged and that the QOL of cancer patients is improved.

Prostaglandins (hereinafter, referred to as PG(s)) are fatty acid derivatives, members of class of organic carboxylic acids, which are contained in tissues or organs of human or other mammals, and exhibit a wide range of physiological activity. PGs found in nature (primary PGs) generally have a prostanoic acid skeleton as shown in the formula (A):

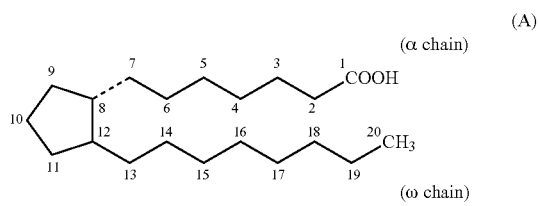

On the other hand, some of synthetic analogues of primary PGs have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:
Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

Some 15-keto (i.e., having oxo at the 15-position instead of hydroxy)-PGs and 13,14-dihydro (i.e., having single bond between the 13 and 14-position)-15-keto-PGs are fatty acid derivatives known as the substances naturally produced by the action of enzymes during the metabolism of primary PGs.

U.S. Patent application publication No. 2006/0281818 to Ueno et al. describes that a specific prostaglandin compound has a significant effect on a conformational change in the TJs that results in recovery of gastrointestinal mucosal barrier function.

DISCLOSURE OF THE INVENTION

An object of the present invention is to provide a method or medicament for achieving higher therapeutic effects against tumor by reducing toxic side effects induced by an anti-tumor agent.

Another object of the present invention is to provide a method or medicament for treating a disease or condition induced by an anti-tumor agent.

A further object of the present invention is to provide a method or medicament for treating mucositis.

The present invention relates to a pharmaceutical combination comprising:
(a) a pharmaceutically effective amount of an anti-tumor agent selected from the group consisting of an alkylating agent, an antimetabolite, an antibiotic, a plant alkaloid, a molecular targeting drug, a hormone, a platinum complex, an antisense, an antibody and RNAi, and (b) a pharmaceutically effective amount of a fatty acid derivative represented by the formula (I):

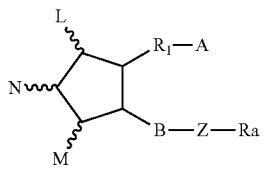

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —COOH or a functional derivative thereof;

B is single bond, —$CH_2$—$CH_2$—, —CH═CH—, —C≡C—, —$CH_2$—$CH_2$—$CH_2$—, —CH═CH—$CH_2$—, —$CH_2$—CH═CH—, —C≡C—$CH_2$— or —$CH_2$—C≡C—;

Z is

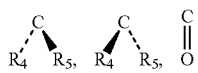

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

By combining an anti-tumor agent and a fatty acid derivative of formula (I), the effect of the anti-tumor agent is augmented and/or the adverse side effect of the anti-tumor agent is well suppressed.

In another aspect of the invention, there is provided a pharmaceutical composition comprising:
(a) a pharmaceutically effective amount of an anti-tumor agent selected from the group consisting of an alkylating agent, an antimetabolite, an antibiotic, a plant alkaloid, a molecular targeting drug, a hormone, a platinum complex, an antisense, an antibody and RNAi and
(b) a pharmaceutically effective amount of a fatty acid derivative represented by the formula (I) in association with a pharmaceutically suitable excipient.

According to the present invention, the composition comprising the two components may be formulated in a single dosage unit that comprises both of components (a) and (b) or separate dosage units that comprise components (a) and (b) separately.

Further, the present invention provides a method for treating a tumor, which comprises administering a combination of:
(a) a pharmaceutically effective amount of an anti-tumor agent selected from the group consisting of an alkylating agent, an antimetabolite, an antibiotic, a plant alkaloid, a molecular targeting drug, a hormone, a platinum complex, an antisense, an antibody and RNAi and
(b) a pharmaceutically effective amount of a fatty acid derivative represented by the formula (I) to a subject in need thereof.

According to the present invention, the components (a) and (b) may be administered simultaneously, separately or sequentially.

Furthermore, the present invention provides a composition for treating a toxic side effect such as gastrointestinal damage including mucositis induced by an anti-tumor agent in a mammalian subject, which comprises a pharmaceutically effective amount of a fatty acid derivative represented by the formula (I), wherein the subject to be treated is receiving the anti-tumor agent that is selected from the group consisting of an alkylating agent, an antimetabolite, an antibiotic, a plant alkaloid, a molecular targeting drug, a hormone, a platinum complex, an antisense, an antibody and RNAi.

Still further, the present invention also provides a composition for treating mucositis such as stomatitis in a mammalian subject that comprises a pharmaceutically effective amount of a fatty acid derivative represented by the formula (I).

DETAILED DESCRIPTION OF THE INVENTION (a) Anti-Tumor Agent

Anti-tumor agent mentioned in the present invention is selected from the group consisting of an alkylating agent, an antimetabolite, an antibiotic, a plant alkaloid, a molecular targeting drug, a hormone, a platinum complex, an antisense, an antibody and RNAi.

Examples of anti-tumor agents are alkylating agents such as cyclophosphamide and buslfan; antimetabolites such as methotrexate, 6-mercaptopurine (6-MP), azathioprine, fluorouracil (5-FU), tegafur and cytosine arabinoside (ara-C); antibiotics such as bleomycin, mitomycin C, daunorubicin, adriamycin and actinomycin D; plant alkaloids such as vincristine, vinblastine, vindesine, paclitaxel, docetaxel, etoposide and irinotecan; molecular targeting drugs such as imatinib, gefinitib, erlotinib, sorafenib, sunitinib, trastuzumab, rituximab, gemtuzumab-ozogamicin, bevacizumab and cetuximab; hormones such as prednisolone, diethylstilbestrol and tamoxifen; platinum complexes such as cisplatin, carboplatin and oxaliplatin; antisenses such as bcl-2 antisense such as G3139, hsp27 antisense such as OGX427, XIAP antisense such as AEG35156, PKC-alpha antisense such as LY900003, hypoxia-induced factor antisense such as EZN-2968; antibodies such as CD20 antibody such as Rituximab, Her2 antibody such as Trastuzumab, VEGF antibody such as Bevacizumab, EGFR antibody such as Cetuximab: RNAi such as RNAi targeted Ribonucleotide reductase such as CALAA-01. Preferable examples of anti-tumor agents include 5-FU, tegafur and cisplatin.

(b) Fatty Acid Derivative

The nomenclature of the fatty acid derivative used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-deoxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of the α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at positions 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

The fatty acid derivative used in the present invention is represented by the formula (I):

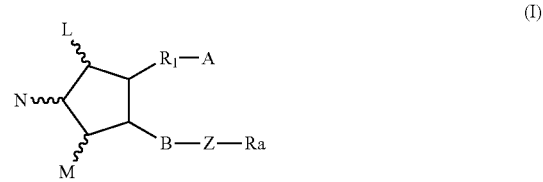

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

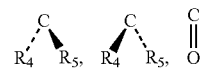

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

A preferred compound used in the present invention is represented by the formula (II):

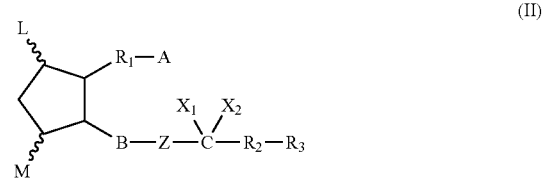

(II)

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

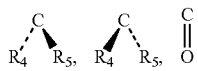

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy(lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydrogen, hydroxy and oxo, and especially, M is hydroxy or hydrogen and L is oxo.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur.

Examples of $R_1$ include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
$CH_2$—$CH_2$—$CH_2$—$CH_2$$CH_2$CH=CH—,
—$CH_2$—C≡C—$CH_2$—$CH_2$—$CH_2$—$CH_2$—,
—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom.

Preferable compounds include Ra is substituted by halogen and/or Z is C=O in the formula (I), or one of X1 and X2 substituted by halogen and/or Z is C=O in the formula (II).

Example of the preferred embodiment is a (−)-7-[(2R,4aR,5R,7aR)-2-(1,1-Difluoropentyl)-2-hydroxy-6-oxooctahydrocyclopenta[b]pyran-5-yl]heptanoic acid, (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid and (−)-7-[(1R,2R)-2-(4,4-difluoro-3-oxooctyl)-5-oxocyclopentyl]heptanoic acid or its functional derivative thereof.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the fatty acid derivative which is dihydro between 13 and 14, and keto(=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the fatty acid derivatives used in the invention include the bicyclic compound and analogs or derivatives thereof.

The bicyclic compound is represented by the formula (III)

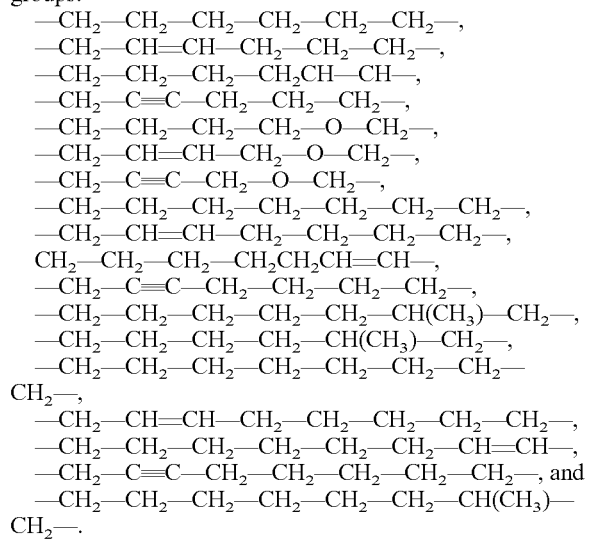

(III)

wherein, A is —$CH_3$, or —$CH_2OH$, —$COCH_2OH$, —COOH or a functional derivative thereof;
$X_1'$ and $X_2'$ are hydrogen, lower alkyl, or halogen;
Y is

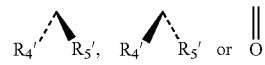

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

Pharmaceutically Suitable Excipient

According to the invention, each of the components of the combination may be formulated in any form together or separately to give a pharmaceutical composition. The pharmaceutically suitable excipient may be, therefore, selected depending on the desired form of the composition. According to the invention, "pharmaceutically suitable excipient" means an inert substance, which is suitable for the form, combined with the active ingredient of the invention.

For example, solid composition for oral administration of the present invention may include tablets, capsules, pills, powders, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, $\alpha,\beta$- or $\gamma$-cyclodextrin; etherified cyclodextrin such as dimethyl-$\alpha$-, dimethyl-$\beta$-, trimethyl-$\beta$-, or hydroxypropyl-$\beta$-cyclodextrin; branched cyclodextrin such as glucosyl-, maltosyl-cyclodextrin; formylated cyclodextrin, cyclodextrin containing sulfur; phospholipid and the like. When the above cyclodextrins are used, an inclusion compound with cyclodextrins may be sometimes formed to enhance stability. Alternatively, phospholipid may be sometimes used to form a liposome, resulting in enhanced stability.

Tablets or pills may be coated with film soluble in the stomach or intestine such as sugar, gelatin, hydroxypropyl cellulose, or hydroxypropylmethyl cellulose phthalate as needed. Further, they may be formed as capsules with absorbable substances such as gelatins. Preferably, the composition is formulated in a soft gelatin capsule with liquid contents of the fatty acid derivative and a medium chain fatty acid triglyceride. Examples of the medium chain fatty acid triglyceride used in the present invention include a triglyceride of a saturated or unsaturated fatty acid having 6-14 carbon atoms which may have a branched chain. A preferred fatty acid is a straight chain saturated fatty acid, for example caproic acid (C6), caprylic acid (C8), capric acid (C10), lauric acid (C12) and myristic acid (C14). In addition, two or more medium chain fatty acid triglycerides may be used in combination. Further suitable excipients are disclosed in WO 01/27099.

A liquid composition for oral administration may be pharmaceutically acceptable emulsion, solution, suspension, syrup, or elixir, as well as generally used inactive diluent. Such composition may contain, in addition to the inactive diluent, adjuvant such as lubricant and suspension, sweetening agent, flavoring agent, preservatives, solubilizers, anti-oxidants and the like. The details of the additives may be selected from those described in any general textbooks in the pharmaceutical field. Such liquid compositions may be directly enclosed in soft capsules. Solutions for parenteral administration, for example, suppository, enema and the like according to the present invention include sterile, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, fatty acid triglyceride, and vegetable oil such as olive oil, alcohols such as ethanol, polysorbate and the like. Such composition may contain adjuvants such as preservatives, wetting agent, emulsifier, dispersant, anti-oxidants and the like.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The composition of the present invention may be in the form of spraying composition, which may be prepared according to a known method.

The composition of the present invention may be in the form of intranasal preparation. Example of the intranasal preparations may be aqueous or oily solutions, suspensions or emulsions comprising one or more active ingredient. For the administration of an active ingredient by inhalation, the composition of the present invention may be in the form of suspension, solution or emulsion which can provide aerosol or in the form of powder suitable for dry powder inhalation. The composition for inhalational administration may further comprise a conventionally used propellant.

Example of the external agent includes all the external preparations used in the fields of dermatology and otolaryngology, which includes ointment, cream, liquids, lotion, patch and spray.

Another form of the composition of the present invention is suppository or pessary, which may be prepared by mixing active ingredients into a conventional base such as cacao butter that softens at body temperature, and nonionic surfactants having suitable softening temperatures may be used to improve absorbability.

According to the method of the invention, the composition of the present invention can be administered systemically or locally by means of oral or parenteral administration, including a suppository, enema and the like. Single or multiple compositions may be administered to achieve the desired dose.

The expression of "administering the combination" or "combination is administered" used herein means both components are administered to a subject simultaneously in the form of a single entity or dosage, or both components are administered to a patient as separate entities either simultaneously or sequentially with no specific time limits, wherein such administration provides therapeutically effective levels of the two components in the body, preferably at the same time.

According to the present invention, tumor in a mammalian subject may be treated by the instant invention by administering the combination of the present invention. The mammalian subject may be any subject including a human patient. The composition may be applied systemically or topically. Usually, the compound may be administered by oral administration, intranasal administration, inhalational administration, intravenous injection (including infusion), subcutaneous injection, intra rectal administration, intra vaginal administration, transdermal administration as well as it may be an external agent including liquid, ointment, paste or patch and the like.

The dose of each component may vary depending on the strain of the animal, age, body weight, symptom to be treated, desired therapeutic effect, administration route, term of treatment and the like. A satisfactory effect can be obtained by systemic administration 1-4 times per day or continuous administration of the combination. The amount of component (a) of the combination may be, for example, about 0.1 to about 100 mg/kg/day, preferably about 0.5 to about 30 mg/kg/day, for tegafur; 0.1 to about 100 mg/kg/day, preferably about 10 to about 40 mg/kg/day for 5-FU; 0.1 to 100 mg/kg/day, preferably 5 to 30 mg/kg/day for cisplatin. The amount of component (b) or a fatty acid derivative of formula (I) may be about 0.00001-500 mg/kg per day, more preferably 0.001-1000 µg/kg per day, and especially 0.01-100 µg/kg per day. The topical formulation of a fatty acid derivative of formula (I) may be 0.000001-10.0%, more preferably 0.00001-5.0% by weight base on the total amount of the composition.

The combination of the present invention can be administered in a single dose or in 2 to 4 divided doses per day. When in the form of an injectable solution for, for example, intravenous injection, the composition, which, if necessary, may be diluted with a physiological saline or injectable glucose solution, can be gradually administered to an adult human subject over 5 minutes or longer. When in the form of a suppository, the composition is administered to an adult human subject once or twice a day at an interval of 6 to 12 hours by insertion into the rectum.

Further, damages induced by an anti-tumor agent in a mammalian subject may be treated by administering the composition comprising a fatty acid derivative of formula (I). In this embodiment, the composition comprising the fatty acid derivative of formula (I) may be prepared and administered in the same manner as discussed above.

The term "treatment" or "treating" used herein includes any means of control such as prevention, care, relief of the condition, attenuation of the condition and arrest of progression.

The types of tumors to be treated by the combination of the present invention are not limited and may be, for example, head and neck cancers, gastrointestinal cancers such as esophageal cancer, gastric cancer, colon cancer, rectal cancer (cancer of the large intestine) and pancreatic cancer, liver cancer, gallbladder/biliary cancer, lung cancer, breast cancer, vesical cancer, prostate cancer, uterine cancer, pharyngeal cancer, renal cancer, ovarian cancer, etc. In particular, a remarkable effect can be expected toward gastrointestinal cancers.

According to the present invention, the antitumor effect of an anti-tumor agent as an active ingredient can be significantly strengthened without notably increasing the toxicity of the same.

In addition, according to the present invention, the fatty acid derivatives are useful for reducing or preventing toxic side effect especially, gastrointestinal damage induced by the anti-tumor agent. The gastrointestinal damages induced by an anti-tumor agent may be mucositis such as stomatitis, enteritis, gastrointestinal ulcer, pancreatitis, heaptic and biliary disorders.

The pharmaceutical composition of the present invention may further contain other pharmacological ingredients as far as they do not contradict the purpose of the present invention.

Further details of the present invention will follow with reference to test example, which, however, is not intended to limit the present invention.

EXAMPLE 1

Effects of Compound a Against 5-FU Induced Toxicity

Methods

After 1 week of acclimatization period, the experiment started (Day 0). Compound A ((−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid) (3, 10, 30 µg/kg) or vehicle was administered orally once daily for 5 days from Day 0 to 4 (Schedule 1).

In other dosing schedule group, Compound A (30 µg/kg) was administered orally once daily from Day 4 to Day 6 (Schedule 2).

5-FU (50 mg/kg) was administered intraperitoneally once daily for 4 days from Day 1 to 4. On Day 1, 2, 3, and 4, 5-FU was administered immediately after administration of Compound A or vehicle. During the experiment period (Day 0-7), animals were weighed every day. On Day 7, the animals were anesthetized by isofluran. Ileum was excised and fixed in 10% formalin. Paraffin-embedded sections were prepared and stained with H&E for histopathological evaluation of tissue damage. The tissue damage was graded according to the following criteria:
 0. No change,
 1: slight,
 2: mild,
 3: moderate,
 4: severe The effect of each compound was evaluated using total score of tissue damage.

Results

The total score of each treatment group is shown in the table below. Compound A decreased total scores at 10 or 30 µg/kg regardless of the dosing schedule. This suggests that Compound A is potent against the toxicity, especially, gastrointestinal toxicity such as mucositis induced by 5-FU.

| Drugs | Dose (µg/kg) | No. of animals examined | Dosing Schedule | Total score |
|---|---|---|---|---|
| No treatment | — | 3 | — | 0.0 |
| Vehicle | — | 3 | 1 | 10.3 |

-continued

| Drugs | Dose (µg/kg) | No. of animals examined | Dosing Schedule | Total score |
|---|---|---|---|---|
| Compound A | 3 | 3 | 1 | 10.0 |
| | 10 | 3 | 1 | 5.0 |
| | 30 | 3 | 1 | 5.7 |
| | 30 | 3 | 2 | 4.3 |

EXAMPLE 2

Effects of Compound A on Stomatitis

Methods

Male Golden Syrian hamsters (5 weeks old) were used. After 1 week acclimatization period, the hamsters were administered intraperitoneally with 60 mg/kg 5-fluorouracil (5-FU) (Day 1). 5-FU administration was repeated again on Day 2. On Day 4, the cheek pouch mucosa of the hamsters is mechanically irritated under anesthesia by superficial scratching with the tip of an 18-gauge needle to produce transient erythema. On Day 8 and 10, the same scratching procedure was conducted and 5-FU administration was done. The Compound A at the doses of 24 µg/site or vehicle was topically applied to the cheek pouches from Day 1 to Day 14. During the treatment, the cheek pouch mucosa was macroscopically observed and the buccal lesion was scored according to the following criteria (stomatitis score):
 0: Normal mucosa
 1: Erythema was observed
 2: Severe erythema was observed
 3: Severe erythema and formation of ulcers in one or more places were observed. Cumulative size of the ulcers involves ~25% of the pouch mucosa. Pseudomembrane formation was evident.
 4: Severe erythema and formation of ulcers were observed. Cumulative size of the ulcers involved about half of the pouch mucosa. Loss of mucosal pliability.
 5: diffuse, extensive ulceration. Loss of mucosal pliability. Pouch could be only partially extracted from mouth.

Severity of stomatitis was evaluated using the mean of scores per treatment group.

Results

Compared to vehicle control group, Compound A improved stomatitis aggravated by 5-FU treatment.

| Group | 5-FU treatment | n | stomatitis score on Day 14 (Mean ± SE) |
|---|---|---|---|
| No treatment | No | 4 | 0 |
| Vehicle control | Yes | 4 | 1.25 ± 0.25 |
| Compound A 24 µg/site | Yes | 4 | 0.25 ± 0.25* |

*$p < 0.05$ vs. vehicle control group (student's t-test)

What is claimed is:

1. A method for treating oral mucositis induced by an anti-tumor agent in a mammalian subject, which comprises administering a pharmaceutically effective amount of (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid to the subject in need thereof, wherein the subject is receiving the anti-tumor agent that is selected from the group consisting of an alkylating agent, an antimetabolite, an antibiotic, a plant alkaloid, a molecular targeting drug, a hormone, a platinum complex, an antisense, an antibody and RNAi,
 wherein the molecular targeting drug is selected from the group consisting of imatinib, gefinitib, erlotinib, sorafenib, sunitinib, trastuzumab, rituximab, gemtuzumab-ozogamicin, bevacizumab and cetuximab, the hormone is selected from group consisting of prednisolone, diethylstilbestrol and tamoxifen, the antisense is selected from the group consisting of bcl-2 antisense, hsp27 antisense, XIAP antisense, PKC-alpha antisense and hypoxia-induced factor antisense, the antibody is selected from the group consisting of CD20 antibody, Her2 antibody, VEGF antibody and EGFR antibody, and the RNAi is RNAi targeted Ribonucleotide reductase.

2. The method as described in claim 1, wherein said anti-tumor agent is 5-FU or tegafur.

3. The method as described in claim 1, wherein said anti-tumor agent is cisplatin.

4. The method as described in claim 1, wherein the oral mucositis is stomatitis.

5. The method as described in claim 1, wherein the anti-tumor agent is selected from the group consisting of an alkylating agent, an antimetabolite, an antibiotic and a plant alkaloid.

* * * * *